United States Patent [19]

Garrod et al.

[11] 4,221,582
[45] Sep. 9, 1980

[54] PLANT GROWTH REGULATING COMPOUNDS, COMPOSITIONS AND METHODS

[75] Inventors: John F. Garrod, Draycott; Douglas Greenwood, Nottingham; Leonard G. Copping, Southwell; Robert F. Brookes, Tollerton, all of England

[73] Assignee: The Boots Company Limited, Nottingham, England

[21] Appl. No.: 892,558

[22] Filed: Apr. 3, 1978

[30] Foreign Application Priority Data

Apr. 5, 1977 [GB] United Kingdom ............... 14243/77

[51] Int. Cl.² ........................ A01N 5/00; A01N 9/00; A01N 9/12; C07D 265/30
[52] U.S. Cl. ........................................ 71/76; 71/88; 71/98; 544/158
[58] Field of Search ............... 71/76, 98, 88; 544/158

[56] References Cited

U.S. PATENT DOCUMENTS

| | | | |
|---|---|---|---|
| 3,133,947 | 5/1974 | Tilles | 544/158 |
| 3,235,356 | 2/1966 | Herschler | 71/98 |
| 3,282,979 | 11/1966 | Reifschneider et al. | 71/98 |
| 3,303,209 | 2/1967 | Reipschneider et al. | 71/98 |
| 3,652,255 | 3/1972 | Osieka et al. | 71/98 |
| 3,784,563 | 1/1974 | Emerson et al. | 544/158 |
| 3,834,888 | 9/1974 | George et al. | 71/76 |
| 3,856,501 | 12/1974 | Zeeh et al. | 71/76 |
| 3,975,180 | 8/1976 | Gozzo et al. | 71/88 |

FOREIGN PATENT DOCUMENTS

| | | | |
|---|---|---|---|
| 5063135 | 5/1975 | Japan | 71/88 |
| 5115627 | 7/1976 | Japan | 71/76 |
| 407644 | 9/1966 | Switzerland | 71/98 |

OTHER PUBLICATIONS

Wirwillie et al., "Six New Plant-Growth-Inhibiting, etc.," (1950).

Primary Examiner—Glennon H. Hollrah
Attorney, Agent, or Firm—Lawrence Rosen; E. Janet Berry

[57] ABSTRACT

New compounds are described which are of value for regulating of plant growth, as well as compositions containing them and methods of using them, are described. The compounds have the formula:

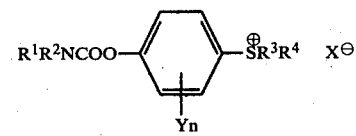

in which $R^1$ and $R^2$ are each alkyl, alkenyl, alkynyl, cycloalkyl or optionally substituted phenyl or together with the nitrogen atom to which they are attached from a heterocyclic ring, Y is alkyl, alkoxy or halo, n is 0 or an integer 1 to 3, $R^3$ and $R^4$ are each methyl or ethyl, and X is one equivalent of an anion.

10 Claims, No Drawings

PLANT GROWTH REGULATING COMPOUNDS, COMPOSITIONS AND METHODS

This invention relates to new compounds and their use in regulating plant growth.

The invention comprises compounds of the formula

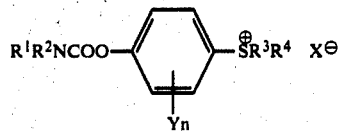

in which $R^1$ and $R^2$ are each alkyl, alkenyl, alkynyl, cycloalkyl or optionally substituted phenyl or together with the nitrogen atom to which they are attached form a heterocyclic ring, Y is alkyl, alkoxy or halo, n is 0 or an integer 1 to 3, $R^3$ and $R^4$ are each methyl or ethyl, and X is one equivalent of an anion.

We have found that these compounds are effective in controlling the growth of a wide variety of crops and accordingly the invention includes a method of controlling plant growth by applying to the plant a growth-regulating amount of a compound of formula I. The method of the invention is especially applicable for controlling the growth of dicotyledonous crops such as for example cotton, sunflowers, pot plants such as chrysanthemums, and legumes such as peanuts, beans and particularly soybeans. The active ingredient can be applied in any convenient way that allows uptake by the plant, for instance, by spraying, application of granules to the soil, or when appropriate, by irrigation methods. Preferably it is applied directly to the growing plant by means of a foliar spray technique. Treatment takes place at a stage when growth regulation, generally a retardation effect, results in an improvement in crop production. This can take the form of increased crop yield, in the case of for example soybean, or an improvement in crop management when, for example, a reduction in stem length of sunflowers and pot plants results in greater ease of handling.

In formula I above $R^1$ and $R^2$ can be the same or different and are each alkyl, alkenyl, alkynyl, cycloalkyl or optionally substituted phenyl or together with the nitrogen atom to which they are attached form a heterocyclic ring. When $R^1$ or $R^2$ is alkyl it can be straight or branched chain. Preferably the alkyl group contains up to 10 carbon atoms, typical examples including methyl, ethyl, propyl, isopropyl, butyl, isobutyl, sec.butyl, tert. butyl, pentyl, hexyl, heptyl, octyl, nonyl and decyl. A preferred alkyl group is one containing from 1 to 4 carbon atoms especially for example methyl.

When $R^1$ or $R^2$ is alkenyl it preferably contains 3 or 4 carbon atoms and can be straight or branched chain. Examples include alkyl, 2-methylallyl, 1-propenyl and 3-butenyl, the most preferred group being allyl. $R^1$ and $R^2$ can also be straight or branched chain alkynyl, especially an alkynyl group containing 3 to 5 carbon atoms, and examples of such groups include prop-2-ynyl and 1,1-dimethylprop-2-ynyl. In addition $R^1$ or $R^2$ can be cycloalkyl which preferably contains 5 to 7 carbon atoms in the ring and is optionally substituted with one to three lower alkyl (especially methyl) groups. Preferred groups are cyclopentyl and cyclohexyl.

The groups $R^1$ or $R^2$ can also be phenyl optionally substituted in the phenyl nucleus with one or more substituents which are the same or different and are halo, alkoxy, alkyl, nitro, trihalomethyl, cyano, alkylthio, nitro or alkylsulphonyl. A preferred group is substituted with one to three substituents, the same or different, which are halo (for example fluoro, chloro and bromo), alkoxy containing 1 or 2 carbon atoms, alkyl containing 1 to 4 carbon atoms, trifluoromethyl or cyano.

As a further alternative $R^1$ and $R^2$, together with the nitrogen atom to which they are attached, can form a heterocyclic ring such as for example morpholino, 1-pyrrolidinyl or piperidino. If desired the heterocyclic ring can be substituted by for example, 1 to 4 ower alkyl (preferably methyl) substituents. Especially preferred heterocyclic groups are piperidino and morpholino.

In addition to the $R^1R^2NCOO-$ and X groups attached to the phenyl nucleus there can be up to three further substituents indicated by the letter Y in formula I above. When there is more than one Y substituent on the phenyl nucleus the substituents need not be identical. Y can be alkyl, alkoxy or halo and when it is alkyl preferably contains 1 to 4 carbon atoms such as for example, methyl, ethyl, isopropyl and tert.butyl. An alkoxy substituent preferably contains 1 or 2 carbon atoms and is either ethoxy or methoxy and a halo group can be fluorine, chlorine, bromine or iodine. It is preferred that n is 2 or 3 and Y is alkyl especially methyl or isopropyl.

As described in formula I, the group $R^3R^4S^{\oplus}-$ is associated with an anion which is preferably one having a single negative charge, a monovalent anion. Examples of preferred non-phytotoxic anions are nitrate, thiocyanate, perchlorate, picrate, tetrafluoroborate, halide for example chloride or bromide, alkyl sulphate for example methyl sulphate, or alkyl or aryl sulphonate for example methanesulphonate, benzenesulphonate. Most conveniently the anion is methyl sulphate or p-toluenesulphonate.

A preferred group of compounds is one in which both $R^1$ and $R^2$ are methyl or $R^1$ and $R^2$ together with the nitrogen atom to which they are attached, form a piperidino or morpholino group. It is also preferred that Y is methyl and n is 2. Preferably $R^3$ and $R^4$ are both methyl and X is methyl sulphate or p-toluenesulphonate. Two particularly preferred compounds are (4-pentamethylenecarbamoyloxy-2,5-dimethylphenyl)dimethylsulphonium p-toluenesulphonate and [4-(3-oxapentamethylenecarbamoyloxy)-2,5-dimethylphenyl]dimethylsulphonium methyl sulphate which have, respectively, the structures

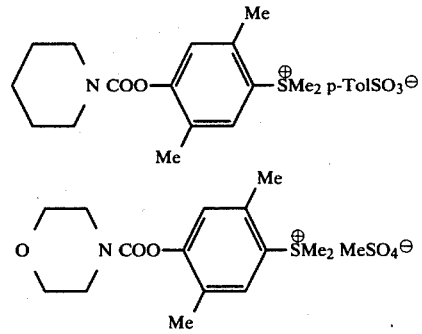

In addition the invention comprises a crop growth regulating composition comprising a compound of formula I together with a diluent or carrier. The diluent or carrier can be solid or a liquid, optionally in association with a surface active agent. The active compound can be employed as a wide variety of formulations, for example, a solution, a dispersion, a soluble powder, a dispersible powder or granules.

Preferred formualtions are solutions and soluble powders. Solutions, preferably in water, can be of an appropriate concentrate for direct application to the crop or they can be in the form of a concentrated primary composition, for example, a concentrated aqueous solution which requires dilution with a suitable quantity of water or other diluent before application. A concentrated aqueous solution can also contain a small quantity of a suitable agent to prevent foaming.

Such concentrated primary compositions are a convenient way of supplying the consumer, and a further example is a soluble powder formulation which comprises the active compound in powder form optionally together with a humectant or flow agent, for example, silica.

As a dispersion, the composition of the invention comprises an active compound dispersed in a liquid medium together with a dispersing agent. Such dispersions can be prepared from a dispersible powder comprising an active compound and a dispersing agent.

A granular solid comprises an active compound associated with a solid powdery diluent, for example kaolin, the mixture being granulated by known methods. Alternatively it comprises the active compound coated or adsorbed on a pre-formed granular diluent, for example, fuller's earth, attapulgite or limestone grit.

The concentration of the active compound in the composition of the invention can vary widely. In the case of a concentrated primary composition it is preferably from 15 to 95 percent by weight. For example a concentrated aqueous solution may contain from 20 to 50 percent by weight, the concentration depending on the solubility of the compound, and a soluble powder will preferably contain 50 to 95 percent by weight. The concentration of active compound in a composition intented for direct application to a crop preferably comprises from 0.001 to 10 percent, more especially from 0.005 to 5 percent by weight, although when aerial spraying of a crop is contemplated compositions having a higher concentration, for instance, up to 30 percent by weight may be chosen in preference.

Also included in the invention is a method for regulating the growth of a crop which comprises applying a growth-regulating amount of a compound of the invention to the crop. The active compound is usually best applied during the vegetative stages of grwoth and preferably at an application rate of 0.02 to 20 kilograms per hectare for example 0.1 to 15 kilograms per hectare. In the case of crops such as legumes, cotton and sunflowers, application preferably takes place during the late vegetative stage of growth, for example, just prior to or just after the onset of flowering. In the case of pot plants earlier application, during the early vegetative stage of growth, is more appropriate.

As indicated above the compounds have been observed to show a wide variety of growth-regulating activity on a range of crops. An example of the invention is a method of controlling the growth of soybeans by application of a compound of the invention to the growing crop. Treatment of soybeans, for example, at about the four true leaf stage, curbs vegetative growth to an extent that assists crop cultivation and helps prevent lodging. Application at a later stage, for example at the onset of flowering, has been found to increase the yield of the crop.

Further aspects of the method of the invention relate to the production of cotton and soybean crops both of which are preferably treated when the plants are actively making vegetative growth. As a result, growth is curbed and this lagter enables the crop to be collected more easily at a harvest time. A further example of the invention is a method of controlling the growth of sunflowers, which are most suitably treated at the 4 to 12 leaf stage when the stem is actively growing, in order to increase yield and to shorten stem length. Controlling the size of pot plants, especially chrysanthemums, leads to a smaller, more compact plant, which is more easily handled and attractive to the purchaser. In the case of chrysanthemums treatment preferably takes place at an early stage for example within one and four weeks after pinching.

More than one active compound can, of course, be employed in the method of the invention. In addition further crop regulators or other active ingredients, for example, compounds known to possess herbicidal, fungicidal insecticidal or acaricidal properties can be used together with the active compound of the invention.

The compounds of the invention can be prepared by a process which comprises reacting a compound of the formula

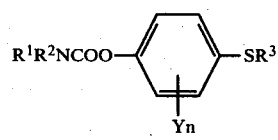

II in which the symbols have the meanings given them above, with an alkylating agent of the formula $R^4X$ where X is the radical of a strong acid, for example, sulphuric or toluene sulphonic acid. If it is desired to produce other salts, this can be followed by the further step of replacing the strong acid anion by other ions in a precipitation reaction, for example, by reacting a concentrated aqueous solution of the quaternary methyl sulphate with a concentrated aqueous solution of an alkali metal salt. The first reaction can be carried out in the presence of an organic solvent such as for example nitrobenzene although this can be dispensed with when the alkylating agent is itself a solvent. Preferably the reaction is performed at a temperature of from 10° to 120° C.

In their turn, compounds of formula II can be prepared by reacting a compound of the formula

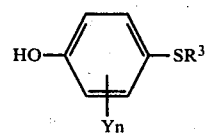

III with a compound of the formula $R^1R^2NCOZ$, where Z is halogen and especially chlorine. The reaction is preferably carried out in an organic solvent which acts as an acid acceptor, such as for example pyridine, and at a temperature of from 50° to 150° C. Compounds of formula III can be prepared by reacting a phenol of the formula

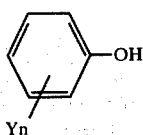

IV with the appropriate dialkyl sulphoxide and hydrogen halide to give a phenyldialkylsulphonium halide, followed by pyrolysis. If desired the pyrolysis step can be dispensed with and the phenyldialkylsulphonium halide directly reacted with $R^1R^2NCOZ$ to obtain compounds of formula II above. Alternatively compounds of formula III can be prepared by reacting a phenol of formula IV with a dialkyl disulphide in the presence of a halogenating agent such as for example sulphuryl chloride.

EXAMPLE 1

This Example illustrates the preparation of compounds according to the invention.

A mixture of 337.5 g thymol, 105 g dimethyl disulphide and 150 ml dry, alcohol-free, chloroform was stirred at $-5°$ to $0°$ C., while 118 g sulphuryl chloride was slowly added over a period of $2\frac{1}{2}$ hours. The solution was stirred for an hour at $10°$ C. warmed over two hours to $60°$ C. with evolution of hydrogen chloride, and then distilled. After removal of the chloroform and excess dimethyl disulphide at the water-pump the pressure was further reduced to remove unchanged thymol and then the product distilled over. On redistillation 2-isopropyl-5-methyl-4-(methylthio)phenol was collected, boiling point $110°-112°$ C. at 0.4 mm.

A mixture of 29.4 g of the above phenol, and 27 g piperidinocarbonyl chloride in 63 ml dry pyridine was heated on a steam bath for 24 hours. The reaction mixture was added to excess of ice-cold dilute hydrochloric acid with formation of an oily product. This was extracted into ether, washed three times with cold dilute sodium hydroxide, once with water, and then dried. The ether was removed by evaporation to give 4-pentamethylenecarbamoyloxy-2-methyl-5-isopropylphenyl methyl sulphide, boiling point $178°-181°$ 1 C. at 0.9 mm. This oily product crystallised on standing and the melting point determined after recrystallisation was $69°-70°$ C.

7.7 g Of the above sulphide and 5.0 ml dimethylsulphate were heated on a steam-bath for five hours. On cooling the solid product was isolated, triturated with dry ether, filtered and recrystallised by dissolving it in methanol followed by precipitation with dry either to give (4-pentamethylenecarbamoyloxy-2-methyl-5-isopropylphenyl)-dimethylsulphonium methyl sulphate, melting point $125°-130°$ C. A satisfactory elemental analysis was obtained.

The following novel compounds were prepared in a similar manner to that described above.

(4-dimethylcarbamoyloxyphenyl)dimethylsulphonium methyl sulphate, m.p. $90°-105°$ C.

(4-dimethylcarbamoyloxy-2,6-dimethylphenyl)dimethylsulphonium methyl sulphate, m.p. $165°-167°$ C.

(4-pentamethylenecarbamoyloxy-2,6-dimethylphenyl)-dimethylsulphonium methyl sulphate, m.p. $147°-150°$ C.

(4-dimethylcarbamoyloxy-2,3,6-trimethylphenyl)dimethylsulphonium methyl sulphate, m.p. $125°-145°$ C.

(4-dimethylcarbamoyloxy-2-methylphenyl)dimethylsulphonium methyl sulphate, m.p. $120°-130°$ C.

(4-dimethylcarbamoyloxy-2,3-dimethylphenyl)dimethylsulphonium methyl sulphate, m.p. $90°-100°$ C.

(4-dimethylcarbamoyloxy-3,5-dimethylphenyl)dimethylsulphonium methyl sulphate, m.p. $140°-143°$ C.

(4-dimethylcarbamoyloxy-2-methyl-5-isopropylphenyl)dimethylsulphonium methyl sulphate m.p. $168°-171°$ C.

(4-dimethylcarbamoyloxy-2-methyl-5-t.butylphenyl)-dimethylsulphonium methyl sulphate, m.p. $96°-100°$ C.

(4-dimethylcarbamoyloxy-3-s-butylphenyl)dimethylsulphonium methyl sulphate, m.p. $80°-95°$ C.

(4-dimethylcarbamoyloxy-3,5-dimethoxyphenyl)dimethylsulphonium methyl sulphate, m.p. $178°-188°$ C.

(4-dimethylcarbamoyloxy-2-methoxyphenyl)dimethylsulphonium methyl sulphate, m.p. $72°-78°$ C.

(4-dimethylcarbamoyloxy-2,3,5-trimethylphenyl)dimethylsulphonium methyl sulphate, m.p. $170°-175°$ C.

(4-dimethylcarbamoyloxy-2-t.butylphenyl)dimethylsulphonium methyl sulphate, m.p. $123°-126°$ C.

(4-diethylcarbamoyloxy-2,5-dimethylphenyl)dimethylsulphonium methyl sulphate, a gum.

(4-diallylcarbamoyloxy-2,5-dimethylphenyl)dimethylsulphonium methyl sulphate, m.p. $78°-82°$ C.

(4-N-methyl-N-phenylcarbamoyloxy-2,5-dimethylphenyl)dimethylsulphonium methyl sulphate, m.p. $131°-134°$ C.

(4-pentamethylenecarbamoyloxy-2,5-dimethylphenyl)-dimethylsulphonium methyl sulphate, m.p. $118°-123°$ C.

(4-N-allyl-N-ethylcarbamoyloxy-2,5-dimethylphenyl)-dimethylsulphonium methyl sulphate, an oil.

(4-N-ethyl-N-propylcarbamoyloxy-2,5-dimethylphenyl)dimethysulphonium methyl sulphate, a gum.

(4-diphenylcarbamoyloxy-2,5-dimethylphenyl)dimethylsulphonium methyl sulphate, m.p. $70°-75°$ C.

S-(4-dimethylcarbamoyloxy-2,5-dimethylphenyl)-S-ethyl-S-methylsulphonium ethyl sulphate, m.p. $85°-95°$ C.

(4-dimethylcarbamoyloxy-2,5-dimethylphenyl)dimethylsulphonium p-toluenesulphonate, m.p. $130°-135°$ C.

S-(4-dimethylcarbamoyloxy-2,5-dimethylphenyl)-S-ethyl-S-methylsulphonium p-toluenesulphonate, m.p. $105°-120°$ C.

(4-dimethylcarbamoyloxy-2,5-di-t.butylphenyl)dimethylsulphonium methyl sulphate, m.p. $203°$ C.

(4-N-4-methoxyphenyl-N-methylcarbamoyloxy-2,5-dimethylphenyldimethylsulphonium methyl sulphate, a gum.

(4-N-ethyl-N-4-fluorophenylcarbamoyloxy-2,5-dimethylphenyl)dimethylsulphonium methyl sulphate, m.p. $170°-172°$ C.

(4-N-butyl-N-4-chlorophenylcarbamoyloxy-2,5-dimethylphenyl)dimethylsulphonium methyl sulphate, m.p. $170°$ C.

(4-dimethylcarbamoyloxy-2,5-dimethylphenyl)diethylsulphonium ethyl sulphate, m.p. $156°-158°$ C.

(4-N-allyl-N-ethylcarbamoyloxy-3,5-dimethylphenyl)-dimethylsulphonium methyl sulphate, m.p. $156°-158°$ C.

(4-N-methyl-N-phenylcarbamoyloxy-3,5-dimethylphenyl)dimethylsulphonium methyl sulphate, m.p. $153°$ C.

(4-N-ethyl-N-propylcarbamoyloxy-3,5-dimethylphenyl)dimethylsulphonium methyl sulphate, m.p. 160°–163° C.
(4-N-octyl-N-phenylcarbamoyloxy-3,5-dimethylphenyl)dimethylsulphonium methyl sulphate, m.p. 124°–125° C.
[4-(2,4-dimethyl-3-oxapentamethylenecarbamoyloxy)-2,5-dimethylphenyl]dimethylsulphonium methyl sulphate, m.p. 149°–157° C.
(4-diethylcarbamoyloxy-3,5-dimethylphenyl)dimethylsulphonium methyl sulphate, m.p. 178°–180° C.
(4-dimethylcarbamoyloxy-2-methoxy-5-chlorophenyl)dimethylsulphonium methyl sulphate, m.p. 165°–170° C.
(4-N-1,1-dimethylprop-2-ynyl-N-propylcarbamoyloxy-2,5-dimethylphenyl)dimethylsulphonium methyl sulphate, m.p. 137° C.
S-(4-pentamethylenecarbamoyloxy-2,5-dimethylphenyl)-S-ethyl-S-methylsulphonium ethyl sulphate, m.p. 120°–130° C.
(4-dicyclohexylcarbamoyloxy-2,5-dimethylphenyl)dimethylsulphonium methyl sulphate, a sticky solid.
(4-N-cyclohexyl-N-methylcarbamoyloxy-2,5-dimethylphenyl)dimethylsulphonium methyl sulphate, m.p. 118°–120° C.
(4-cyclohexyl-N-phenylcarbamoyloxy-2,5-dimethylphenyl)dimethylsulphonium methyl sulphate, m.p. 165°–167° C.
(4-dimethylcarbamoyloxy-3-chloro-5-methylphenyl)dimethylsulphonium methyl sulphate, m.p. 130°–140° C.
(4-pentamethylenecarbamoyloxy-2,3,5-trimethylphenyl)dimethylsulphonium methyl sulphate, a sticky solid.
(4-pentamethylenecarbamoyloxy-3,5-dimethylphenyl)dimethylsulphonium methyl sulphate, m.p. 232° C.
[4-(3-oxapentamethylenecarbamoyloxy)-3,5-dimethylphenyl]dimethylsulphonium methyl sulphate, m.p. 188°–189° C.
(4-tetramethylenecarbamoyloxy-2,5-dimethylphenyl)dimethylsulphonium methyl sulphate, m.p. 165° C.
(4-pentamethylenecarbamoyloxy-2,5-dimethylphenyl)dimethylsulphonium p-nitrobenzenesulphonate, m.p. 187°–189° C.
(4-N-methyl-N-cyclopentylcarbamoylozy-2,5-dimethylphenyl)dimethylsulphonium methyl sulphate, m.p. 145°–146° C.
[4-(3-oxapentamethylenecarbamoyloxy)-2,5-dimethylphenyl]dimethylsulphonium p-toluenesulphonate, m.p. 150°–153° C.
[4-(3-oxapentamethylenecarbamoyloxy)-2,5-dimethylphenyl]dimethylsulphonium benzenesulphonate, m.p. 145°–146° C.
(4-pentamethylenecarbamoyloxy-2,5-dimethylphenyl)dimethylsulphonium benzenesulphonate, m.p. 156°–157° C.
[4-(3-oxapentamethylenecarbamoyloxy-2,5-dimethylphenyl]dimethylsulphonium methanesulphonate, m.p. 157°–158° C.
(4-pentamethylenecarbamoyloxy-2,5-dimethylphenyl)dimethylsulphonium methanesulphonate, m.p. 160° C.
(4-tetramethylenecarbamoyloxy-2,5-dimethylphenyl)dimethylsulphonium p-toluenesulphonate, m.p. 158°–159° C.
[4-(3-oxapentamethylenecarbamoyloxy)-2,5-dimethylphenyl]dimethylsulphonium p-nitrobenzenesulphonate, m.p. 172°–173° C.
(4-pentamethylenecarbamoyloxy-2,5-dimethylphenyl)dimethylsulphonium tetrafluoroborate, m.p. 179°–180° C.
(4-pentamethylenecarbamoyloxy-2,5-dimethylphenyl)dimethylsulphonium pictrate, m.p. 158°–159° C.
(4-pentamethylenecarbamoyloxy-2,5-dimethylphenyl)dimethylsulphonium perchlorate, m.p. 205°–208° C.
(4-pentamethylenecarbamoyloxy-2,5-dimethylphenyl)dimethylsulphonium thiocyanate, m.p. 92°–93° C.
(4-pentamethylenecarbamoyloxy-2,5-dimethylphenyl)dimethylsulphonium iodide, m.p. 88° C.
(4-pentamethylenecarbamoyloxy-2,5-dimethylphenyl)dimethylsulphonium nitrate, m.p. 121°–123° C.

Satisfactory elemental analyses were obtained for all of the above compounds. Many of the compounds decomposed at the melting point.

In the course of preparing the above compounds intermediates of the following structure were isolated.

ZCOO—(phenyl ring with positions 2, 3, 5, 6, Yn)—SMe

| Yn | Z | Physical Constant |
|---|---|---|
| — | NMe$_2$ | 59°–60° C. |
| 2-Me-5-isopropyl Ph | NMe$_2$ | 78°–79° C. |
| 2,6-diMe | NMe$_2$ | 140° C./0.5 mm. |
| 2,6-diMe | piperidino | 37°–39° C. |
| 2,3,6-triMe | NMe$_2$ | 142°–152° C./0.5 mm. |
| 2-Me | NMe$_2$ | 65°–67° C. |
| 2,3-diMe | NMe$_2$ | 77°–79° C. |
| 3,5-diMe | NMe$_2$ | 62°–64° C. |
| 2-Me-5-t.butyl | NMe$_2$ | 64°–69° C. |
| 3-s.butyl | NMe$_2$ | 136° C./0.25 mm. |
| 3,5-diMeO | NMe$_2$ | 163°–164° C. |
| 2-MeO | NMe$_2$ | 90°–92° C. |
| 2,3,5-triMe | NMe$_2$ | 94°–95° C. |
| 2-t.butyl | NMe$_2$ | 48°–49° C. |
| 2,5-diMe | NMe$_2$ | 155°–160° C./0.3–0.5 mm. |
| 2,5-diMe | N(allyl)$_2$ | 164°–173° C./0.3 mm. |
| 2,5-diMe | N(Me)Ph | 84°–86° C. |
| 2,5-diMe | piperidino | 57°–59° C. |
| 2,5-diMe | N(Et)allyl | 157°–162° C./0.3 mm. |
| 2,5-diMe | N(Et)Pr | 136°–137° C./0.1 mm. |
| 2,5-diMe | N(Ph)$_2$ | 119°–120° C. |
| 2,5-dit.butyl | NMe$_2$ | 128°–129° C. |
| 2,5-diMe | N(Me)4MeOPh | 204°–206° C./0.3 mm. |
| 2,5-diMe | N(Et)4FPh | 92°–93° C. |
| 2,5-diMe | N(butyl)4ClPh | 92°–93.5° C. |
| 3,5-diMe | N(Et)allyl | 140° C./0.1 mm. |
| 3,5-diMe | n(Me)Ph | 83°–85° C. |
| 3,5-diMe | N(Et)Pr | 152°–160° C./0.3 mm. |
| 3,5-diMe | N(Ph)octyl | 47°–52° C. |
| 2,5-diMe | morpholino | 87° C. |
| 2,5-diMe | 2,4-dimethyl-morpholino | 44°–47° C. |
| 3,5-diMe | NEt$_2$ | 142°–148° C./0.2 mm. |
| 2MeO-5Cl | NMe$_2$ | 107°–108° C. |
| 2,5-diMe | N(Pr)1,1-dimethyl-prop-2-ynyl | 162°–168° C. |
| 2,5-diMe | N(cyclohexyl)$_2$ | 134°–135° C. |
| 2,5-diMe | N(Me)cyclohexyl | 72.5°–73° C. |
| 2,5-diMe | N(Ph)cyclohexyl | 110.111° C. |
| 3-Cl-5-Me | NMe$_2$ | 141°–144° C./0.4 mm. |
| 2,3,5-triMe | piperidino | 80°–81° C. |
| 3,5-diMe | piperidino | 62°–64° C. |
| 3,5-diMe | morpholino | 83°–84° C. |
| 2,5-diMe | pyrrolidinyl | 58°–60° C. |
| 2,5-diMe | NMe$_2$(1-ethylthio) | 134° C./0.2 mm. |
| 2,5-diMe | N(Me)cyclopentyl | 168°–172° C./0.15 mm. |

Satisfactory elemental anaylses were obtained for all of the above intermediates. In the above table the symbols have the following meanings:
Me—methyl
Et—ethyl
Pr—propyl
F—fluoro
Cl—chloro
Ph—phenyl

EXAMPLE 2

This Example illustrates an alternative method for the preparation of compounds according to the invention.

A mixture of 61 g 2,5-dimethylphenol, 39 g dimethyl sulphoxide and 40 ml methanol was stirred at a temperature of from 0° to 10° C. while a steam of dry hydrogen chloride was passed into it over a period of two hours. Crystals of (4-hydroxy-2,5-dimethylphenyl)dimethylsulphonium chloride separated out. Addition of 100 ml ether and filtration gave a pink solid which was washed with ether and dried.

The sulphonium chloride thus prepared (68.5 g) was added in portions to a flask heated in an oil bath at 170° C. Pyrolysis took place smoothly with evolution of methyl chloride, and was complete after 45 minutes. The residue crystallised on cooling and was recrystallised from light petroleum (boiling point 80°-100° C.) to give 2,5-dimethyl-4-(methylthio)phenol, melting point 98°-99° C.

A mixture of 25.2 g 2,5-dimethyl-4-(methylthio)-phenol and 20.3 ml dimethylcarbamoyl chloride in 70 ml dry pyridine was heated for 24 hours at 100° C. Addition to excess of ice-cold dilute hydrochloric acid gave an oil. The oil product was extracted into ether and washed three times with cold dilute sodium hydroxide and once with water, dried, and the ether removed by evaporation to give 4-dimethylcarbamoyloxy-2,5-dimethylphenyl methyl sulphide, boiling point 146° C. at 0.6 mm to 150° C. to 0.9 mm.

This product (7.1 g) was heated with 4.5 ml dimethyl sulphate on a steam bath for three hours. The solid residue was triturated with dry ether, filtered and recrystallised by dissolving it in methanol followed by precipitation with ether to give (4-dimethylcarbamoyloxy-2,5-dimethylphenyl)dimethylsulphonium methyl sulphate, melting point 70°-175° C. A satisfactory elemental analysis was obtained.

EXAMPLE 3

This Example illustrates the preparation of (4-pentamethylenecarbamoyloxy-2,5-dimethylphenyl)dimethylsulphonium p-toluenesulphonate.

A mixture of 8.4 g 2,5-dimethyl-4-methylthiophenol (prepared in the manner described in Example 2), 9.3 g piperidinocarbonyl chloride and 25 ml dry pyridine was heated at 95° to 100° C. for 24 hours. The cooled mixture was poured into an excess of cold dilute hydrochloric acid and the oil extracted into ether, using two 150 ml portions.

The combined ethereal extracts were washed with 50 ml water, 25 ml 2 N sodium hydroxide and 150 ml water, before being dried over magnesium sulphate. After filtering off the drying agent, the filtrate was evaporated leaving an oil, 4-pentamethylenecarbamoyloxy-2,5-dimethylphenyl methyl sulphide, boiling point 162° to 168° C. at 0.2 mm.

A mixture of 22.4 g of this compound and 20 g methyl p-toluenesulphonate was heated on a steam-bath for 12 hours. Trituration with dry ether left the product which was purified by several precipitations from absolute ethanol by addition of dry ether. After filtration and drying the pure product was obtained, (4-pentamethylenecarbamoyloxy-2,5-dimethylphenyl)dimethylsulphonium p-toluenesulphonate, melting point 150° to 151° C.

EXAMPLE 4

This Example illustrates the preparation of [4-(3-oxapentamethylenecarbamoyloxy)-2,5-dimethylphenyl]dimethylsulphonium methyl sulphate.

A mixture of 59.2 g 2,5-dimethyl-4-methylthiophenol (prepared in the manner described in Example 2), 59.0 g morpholinocarbonyl chloride and 36 ml dry pyridine was heated cautiously to 200° C. and held at that temperature for 15 minutes under gentle reflux.

After cooling, ether was added and the resultant solution was washed with 2 N sodium hydroxide solution and water before being dried with magnesium sulphate. Evaporation of the solvent left a residue which was recrystallised from 1.5 liters petroleum (boiling point 80° to 100° C.) to give 4-(3-oxapentamethylenecarbamoyloxy)-2,5-dimethylphenyl methyl sulphide, melting point 86° to 87° C.

A mixture of 68.1 g of this compound and 27 ml dimethyl sulphate was heated for a period of five hours. The solid produced was dissolved in 150 ml methanol and the stirred solution diluted with 500 ml dry ether. The product precipitated and was filtered off, washed with a mixture of 15 ml methanol and 50 ml dry ether, then with dry ether, before being dried to give [4-(3-oxapentamethylenecarbamoyloxy)-2,5-dimethylphenyl]dimethylsulphonium methyl sulphonate, melting point 185° to 186° C.

EXAMPLE 5

The following Example shows the growth regulating properties of (4-pentamethylenecarbamoyloxy-2-methylisopropylphenyl)dimethylsulphonium methyl sulphate on soybean.

Aqueous solutions containing the active compound at various concentration levels were sprayed on to the foliage of soybean plants until run-off. The plants were kept in a controlled environment room and at the time of spraying were at the 3 to 4 trifoliate leaf stage. There were nine replicate plants for each treatment and three weeks after treatment the height of the plants was measured. Three separate experiments were carried out:

|     | Quantity of active compound and height (cm) | | | Control height (cm) |
| --- | --- | --- | --- | --- |
| (a) | 2000 ppm 58.3 | | 4000 ppm 54.3 | 82.4 |
| (b) | 250 ppm 28.6 | 500 ppm 21.1 | 1000 ppm 20.9 | 34.6 |
| (c) | 250 ppm 16.7 | 500 ppm 13.6 | 1000 ppm 13.8 | 19.8 |

In the case of experiment (a) a count was made of the number of pods at the time of assessment with the following results

| 2000 ppm | 4000 ppm | Control |
| --- | --- | --- |
| 35.9 | 37.4 | 26.0 |

EXAMPLE 6

Seedlings of sunflower and Mung beans were transferred four days after sowing to individual pots in which the roots of the seedlings were in contact with an aqueous solution of the test compound at a concentration of 100 ppm. The seedlings were grown for a further ten days and their heights measured and compared with control plants.

All of the compounds of the invention described in Examples 1 to 4 gave a reduction of at least 25 percent in height for both plants species, without an observable effect on the health and vigour of the plant.

EXAMPLE 7

The activity of compounds of the invention was tested on chrysanthemums and cotton plants, as follows:

(1) Chrysanthemum cuttings were grown under glass in individual pots and two weeks after pinching were sprayed with aqueous solutions of test compound to run-off. The aqueous solutions contained 2000 parts per million of test compound.

The plants were allowed to grow for a further 40 days when the stem length was measured, a comparison being made with the stem length of control plants that had not been treated with test compound.

(2) Cotton seedlings planted in individual pots and grown under glasshouse conditions were sprayed at the 2 to 3 leaf stage with aqueous solutions of test compound to run-off. The aqueous solution contained 2000 parts per million of test compound.

The plants were allowed to grow for a further 38 days when their height was measured and compared with untreated control plants.

All of the following compounds resulted in a greater than 15 percent reduction in height of the plants in both of tests 1 and 2 above.

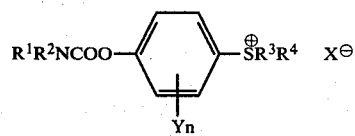

| Z | Yn | X |
|---|---|---|
| piperidino | 2Me-5-iPr | MeSO$_4$ |
| NMe$_2$ | 3,5-diMe | MeSO$_4$ |
| NMe$_2$ | 2,5-diMe | MeSO$_4$ |
| N(allyl)$_2$ | 2,5-diMe | MeSO$_4$ |
| piperidino | 2,5-diMe | MeSO$_4$ |
| piperidino | 2,5-diMe | p-TolSO$_3$ |
| NMe$_2$ | 2,3,5-triMe | MeSO$_4$ |
| morpholino | 2,5-diMe | MeSO$_4$ |
| morpholino | 3,5-diMe | MeSO$_4$ |

EXAMPLE 8

Soybean seedlings in individual pots and grown under glasshouse conditions were sprayed with aqueous solutions of test compound at the 2 to 3 leaf stage of development. In each case the aqueous solution contained 500 parts per million of the test compound and was applied to run-off.

Fifteen days later the height of the plants was measured and a comparison made with control plants which had not been treated with test compound. A percentage reduction of height was calculated and all of the following compounds of the invention caused a greater than 25 percent reduction in height.

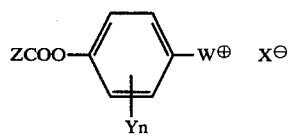

| Z | Yn | W | X |
|---|---|---|---|
| NMe$_2$ | 2,6-diMe | SMe$_2$ | MeSO$_4$ |
| NMe$_2$ | 2Me-5-iPr | SMe$_2$ | MeSO$_4$ |
| piperidino | 2Me-5-iPr | SMe$_2$ | MeSO$_4$ |
| piperidino | 2,6-diMe | SMe$_2$ | MeSO$_4$ |
| NMe$_2$ | 2,3,6-triMe | SMe$_2$ | MeSO$_4$ |
| NMe$_2$ | 2,5-diMe | SMe$_2$ | MeSO$_4$ |
| NMe$_2$ | 3,5-diMe | SMe$_2$ | MeSO$_4$ |
| N(allyl)$_2$ | 2,5-diMe | SMe$_2$ | MeSO$_4$ |
| piperidino | 2,5-diMe | SMe$_2$ | MeSO$_4$ |
| N(Me)Ph | 2,5-diMe | SMe$_2$ | MeSO$_4$ |
| morpholino | 2,5-diMe | SMe$_2$ | PhSO$_3$ |
| morpholino | 2,5-diMe | SMe$_2$ | p-TolSO$_3$ |
| piperidino | 2,3,5-triMe | SMe$_2$ | MeSO$_4$ |
| piperidino | 2,5-diMe | SMe$_2$ | p-TolSO$_3$ |
| NMe$_2$ | 2,3,5-triMe | SMe$_2$ | MeSO$_4$ |
| NMe$_2$ | 2,5-diMe | SMe$_2$ | p-TolSO$_3$ |
| NMe$_2$ | 2,5-diMe | S(Me)Et | p-TolSO$_3$ |
| NMe$_2$ | 2,5-diMe | S(Me)Et | EtSO$_4$ |

What is claimed is:

1. A compound of the formula $$R^1R^2NCOO-\text{(aryl)}_{Y_n}-\overset{\oplus}{S}R^3R^4 \quad X^{\ominus}$$

in which $R^1$ and $R^2$ together with the nitrogen atom to which they are attached form a morpholino ring, Y is $C_1$–$C_4$ alkyl, $C_1$–$C_2$ alkoxy or halo, n is 0 or an integer 1 to 3, $R^3$ and $R^4$ are each methyl or ethyl, and X is one equivalent of a non-phytotoxic anion.

2. A compound according to claim 1 in which Y is methyl.

3. A compound according to either of claims 1 or 2 in which n is 2.

4. A compound according to any of claims 1, 2 or 3 in which $R^3$ and $R^4$ are both methyl.

5. A compound according to any of claims 1, 2, 3, or 4 in which X is methyl sulphate or p-toluenesulphonate.

6. [4-(3-oxapentamethylenecarbamoyloxy)-2,5-dimethylphenyl]dimethylsulphonium methyl sulphate.

7. A crop stunting composition comprising a stunting effective amount of a compound according to claim 1 together with an inert diluent or carrier; said crop being selected from the group consisting of cotton, peanut, sunflower, soybean and pot plants.

8. A composition according to claim 7 in the form of a concentrated aqueous solution containing from 20 to 50 percent by weight of active compound.

9. A composition according to claim 7 in the form of a soluble powder containing from 50 to 95 percent by weight of active compound.

10. A method for stunting the growth of a crop selected from the group consisting of cotton, peanut, sunflower, soybean and pot plants; which comprises applying to the crop a stunting effective amount of a compound as defined in claim 1.

* * * * *